United States Patent
Hunter et al.

(10) Patent No.: US 6,381,485 B1
(45) Date of Patent: Apr. 30, 2002

(54) REGISTRATION OF HUMAN ANATOMY INTEGRATED FOR ELECTROMAGNETIC LOCALIZATION

(75) Inventors: Mark W. Hunter; Paul Kessman, both of Broomfield, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/429,569

(22) Filed: Oct. 28, 1999

(51) Int. Cl.[7] .................................................. A61B 5/05

(52) U.S. Cl. ..................... 600/407; 600/409; 600/415; 600/417; 600/425; 600/429; 606/130; 324/301; 324/302; 324/244

(58) Field of Search ............................... 600/407, 409, 600/415, 417, 428, 429; 606/130; 324/301, 302, 244

(56) References Cited

U.S. PATENT DOCUMENTS

| | | | |
|---|---|---|---|
| 2,650,588 A | 9/1953 | Drew | 128/92 |
| 3,868,565 A | 2/1975 | Kuipers | 324/34 R |
| 3,983,474 A | 9/1976 | Kuipers | 324/43 R |
| 4,054,881 A | 10/1977 | Raab | 343/112 R |
| 4,173,228 A | 11/1979 | Van Steenwyk et al. | 128/653 |
| 4,182,312 A | 1/1980 | Mushabac | 433/68 |
| 4,202,349 A | 5/1980 | Jones | 128/689 |
| 4,314,251 A | 2/1982 | Raab | 343/112 R |
| 4,317,078 A | 2/1982 | Weed et al. | 324/208 |
| 4,339,953 A | 7/1982 | Iwasaki | 73/654 |
| 4,396,945 A | 8/1983 | DiMatteo et al. | 358/107 |
| 4,419,012 A | 12/1983 | Stephenson et al. | 356/141 |
| 4,422,041 A | 12/1983 | Lienau | 324/207 |

(List continued on next page.)

FOREIGN PATENT DOCUMENTS

| | | | |
|---|---|---|---|
| DE | 3717871 C2 | 12/1988 | A61B/19/00 |
| DE | 3717871 A1 | 12/1988 | A61B/19/00 |
| DE | 3838011 A1 | 7/1989 | A61B/19/00 |
| DE | 4225112 C1 | 12/1993 | A61B/19/00 |
| DE | 4233978 | 4/1994 | A61B/19/00 |

(List continued on next page.)

OTHER PUBLICATIONS

Adams, L., et al., Computer–Assisted Surgery, IEEE Computer Graphics & Applications, pp. 43–51 (May 1990).

Adams, L., et al., Aide au Reperage Tridimensionnel pour la Chirurgie de la Base du Crane (Orientation Aid for Head and Neck Surgeons), Innov. Tech. Biol. Med., vol. 13, No. 4, pp. 409–424 (1992).

(List continued on next page.)

Primary Examiner—Marvin M. Lateef
Assistant Examiner—Jeoyuh Lin
(74) Attorney, Agent, or Firm—Harness, Dickey & Pierce, P.L.C.

(57) ABSTRACT

A method for use during a procedure on a body. The method generates a display representing relative positions of two structure during the procedure. The method includes the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

21 Claims, 5 Drawing Sheets

U.S. PATENT DOCUMENTS

| | | | |
|---|---|---|---|
| 4,431,005 A | 2/1984 | McCormick | 128/656 |
| 4,571,834 A | 2/1986 | Fraser et al. | 33/1 PT |
| 4,583,538 A | 4/1986 | Onik et al. | 128/303 B |
| 4,613,866 A | 9/1986 | Blood | 343/448 |
| 4,618,978 A | 10/1986 | Cosman | 378/164 |
| 4,642,786 A | 2/1987 | Hansen | 364/559 |
| 4,649,504 A | 3/1987 | Krouglicof et al. | 364/559 |
| 4,651,732 A | 3/1987 | Frederick | 128/303 R |
| 4,673,352 A | 6/1987 | Hansen | 433/69 |
| 4,722,056 A | 1/1988 | Roberts et al. | 364/413 |
| RE32,619 E * | 3/1988 | Damadian | 128/653 |
| 4,737,794 A | 4/1988 | Jones | 342/448 |
| 4,791,934 A | 12/1988 | Brunnett | 128/653 |
| 4,793,355 A | 12/1988 | Crum et al. | 128/653 |
| 4,821,731 A | 4/1989 | Martinelli et al. | 128/662.06 |
| 4,836,778 A | 6/1989 | Baumrind et al. | 433/69 |
| 4,849,692 A | 7/1989 | Blood | 324/208 |
| 4,896,673 A | 1/1990 | Rose et al. | 128/660.03 |
| 4,905,698 A | 3/1990 | Strohl, Jr. et al. | 128/653 R |
| 4,945,305 A | 7/1990 | Blood | 324/207.17 |
| 4,945,914 A | 8/1990 | Allen | 128/653 R |
| 4,991,579 A | 2/1991 | Allen | 128/653 R |
| 5,016,639 A | 5/1991 | Allen | 128/653 R |
| 5,042,486 A | 8/1991 | Pfeiler et al. | 128/653 R |
| 5,047,036 A | 9/1991 | Koutrouvelis et al. | 606/130 |
| 5,059,789 A | 10/1991 | Salcudean | 250/206.1 |
| 5,078,140 A | 1/1992 | Kwoh | 128/653.1 |
| 5,086,401 A | 2/1992 | Glassman et al. | 395/94 |
| 5,094,241 A | 3/1992 | Allen | 128/653.1 |
| 5,097,839 A | 3/1992 | Allen | 128/653.1 |
| 5,099,845 A | 3/1992 | Besz et al. | 128/653.1 |
| 5,107,839 A | 4/1992 | Houdek et al. | 128/653.1 |
| 5,119,817 A | 6/1992 | Allen | 128/653.1 |
| 5,142,930 A | 9/1992 | Allen et al. | 74/469 |
| 5,152,288 A | 10/1992 | Hoenig et al. | 128/653.1 |
| 5,160,337 A | 11/1992 | Cosman | 606/130 |
| 5,178,164 A | 1/1993 | Allen | 128/898 |
| 5,186,174 A | 2/1993 | Schlondorff et al. | 128/653.1 |
| 5,187,475 A | 2/1993 | Wagener et al. | 340/870.32 |
| 5,193,106 A | 3/1993 | DeSena | 378/673 |
| 5,197,476 A | 3/1993 | Nowacki et al. | 128/660.03 |
| 5,198,877 A | 3/1993 | Schulz | 356/375 |
| 5,211,164 A | 5/1993 | Allen | 128/653.1 |
| 5,211,165 A | 5/1993 | Dumoulin et al. | 128/653.1 |
| 5,214,615 A | 5/1993 | Bauer | 367/128 |
| 5,222,499 A | 6/1993 | Allen et al. | 128/653.1 |
| 5,230,338 A | 7/1993 | Allen et al. | 128/653 |
| 5,230,623 A | 7/1993 | Guthrie et al. | 433/72 |
| 5,249,581 A | 10/1993 | Horbal et al. | 128/664 |
| 5,251,127 A | 10/1993 | Raab | 364/413.13 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,261,404 A | 11/1993 | Mick et al. | 128/653.1 |
| 5,265,610 A | 11/1993 | Darrow et al. | 128/653.1 |
| 5,265,611 A | 11/1993 | Hoenig et al. | 128/653.1 |
| 5,274,551 A | 12/1993 | Corby, Jr. | 364/413.13 |
| 5,279,309 A | 1/1994 | Taylor et al. | 128/782 |
| 5,291,889 A | 3/1994 | Kenet et al. | 128/653.1 |
| 5,295,483 A | 3/1994 | Nowacki et al. | 128/660 |
| 5,299,254 A | 3/1994 | Dancer et al. | 378/163 |
| 5,299,288 A | 3/1994 | Glassman et al. | 395/80 |
| 5,305,203 A | 4/1994 | Raab | 364/413.13 |
| 5,309,913 A | 5/1994 | Kormos et al. | 128/653.1 |
| 5,315,630 A | 5/1994 | Sturm et al. | 378/65 |
| 5,316,024 A | 5/1994 | Hischi et al. | 128/899 |
| 5,318,025 A | 6/1994 | Dumoulin et al. | 128/653.2 |
| 5,325,873 A | 7/1994 | Hirschi et al. | 128/899 |
| 5,353,795 A | 10/1994 | Souza et al. | 128/653.2 |
| 5,353,807 A | 10/1994 | DeMarco | 128/772 |
| 5,359,417 A | 10/1994 | Muller et al. | 356/375 |
| 5,368,030 A | 11/1994 | Zinreich et al. | 128/653.1 |
| 5,371,778 A | 12/1994 | Yanof et al. | 364/413.22 |
| 5,377,678 A | 1/1995 | Dumoulin et al. | 128/653.1 |
| 5,383,454 A | 1/1995 | Bucholz | 128/653.1 |
| 5,389,101 A | 2/1995 | Heilbrun et al. | 606/130 |
| 5,391,199 A | 2/1995 | Ben-Haim | 607/122 |
| 5,397,329 A | 3/1995 | Allen | 606/73 |
| 5,398,684 A | 3/1995 | Hardy | 128/653.1 |
| 5,402,801 A | 4/1995 | Taylor | 128/898 |
| 5,408,409 A | 4/1995 | Glassman et al. | 364/413.13 |
| 5,413,573 A | 5/1995 | Koivukangas | 606/1 |
| 5,419,325 A | 5/1995 | Dumoulin et al. | 128/653.2 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,066 A | 8/1995 | Dumoulin et al. | 128/653.1 |
| 5,443,489 A | 8/1995 | Ben-Haim | 607/115 |
| 5,445,150 A | 8/1995 | Dumoulin et al. | 128/653.1 |
| 5,446,548 A | 8/1995 | Gerig et al. | 356/375 |
| 5,447,154 A | 9/1995 | Cinquin et al. | 128/653.1 |
| 5,453,686 A | 9/1995 | Anderson | 324/207.17 |
| 5,456,718 A | 10/1995 | Szymaitis | 623/11 |
| 5,480,422 A | 1/1996 | Ben-Haim | 607/122 |
| 5,483,961 A | 1/1996 | Kelly et al. | 128/653.1 |
| 5,494,034 A | 2/1996 | Schlöndorff et al. | 128/653.1 |
| 5,515,160 A | 5/1996 | Schulz et al. | 356/241 |
| 5,517,990 A | 5/1996 | Kalfas et al. | 128/653.1 |
| 5,531,227 A | 7/1996 | Schneider | 128/653.1 |
| 5,531,520 A | 7/1996 | Grimson et al. | 382/131 |
| 5,546,951 A | 8/1996 | Ben-Haim | 128/702 |
| 5,551,429 A | 9/1996 | Fitzpatrick et al. | 128/653.1 |
| 5,558,091 A | 9/1996 | Acker et al. | 128/653.1 |
| 5,568,809 A | 10/1996 | Ben-haim | 128/656 |
| 5,572,999 A | 11/1996 | Funda et al. | 128/653.1 |
| 5,575,798 A | 11/1996 | Koutrouvelis | 606/130 |
| 5,383,454 C1 | 12/1996 | Bucholz | 128/653.1 |
| 5,588,430 A | 12/1996 | Bova et al. | 128/653.1 |
| 5,590,215 A | 12/1996 | Allen | 382/128 |
| 5,592,939 A | 1/1997 | Martinelli | 128/653.1 |
| 5,595,193 A | 1/1997 | Walus et al. | 128/898 |
| 5,600,330 A | 2/1997 | Blood | 342/463 |
| 5,603,318 A | 2/1997 | Heilbrun et al. | 128/630 |
| 5,611,025 A | 3/1997 | Lorensen et al. | 395/119 |
| 5,617,857 A | 4/1997 | Chader et al. | 128/653.1 |
| 5,622,169 A | 4/1997 | Golden et al. | 128/653.1 |
| 5,622,170 A | 4/1997 | Schulz | 128/653.1 |
| 5,630,431 A | 5/1997 | Taylor | 128/897 |
| 5,638,819 A | 6/1997 | Manwaring et al. | 128/653.1 |
| 5,640,170 A | 6/1997 | Anderson | 343/895 |
| 5,645,065 A | 7/1997 | Shapiro et al. | 128/653.1 |
| 5,647,361 A | 7/1997 | Damadian | 128/683.2 |
| 5,662,111 A | 9/1997 | Cosman | 128/653.1 |
| 5,676,673 A | 10/1997 | Ferre et al. | 606/130 |
| 5,681,260 A | 10/1997 | Ueda et al. | 600/114 |
| 5,682,886 A | 11/1997 | Delp et al. | 128/653.1 |
| 5,682,890 A | 11/1997 | Kormos et al. | 128/653.2 |
| 5,694,945 A | 12/1997 | Ben-Haim | 128/736 |
| 5,695,500 A | 12/1997 | Taylor et al. | 606/130 |
| 5,695,501 A | 12/1997 | Carol et al. | 606/130 |
| 5,697,377 A | 12/1997 | Wittkampf | 128/696 |
| 5,711,299 A | 1/1998 | Manwaring et al. | 128/653.1 |
| 5,713,946 A | 2/1998 | Ben-Haim | 607/122 |
| 5,715,822 A | 2/1998 | Watkins et al. | 128/653.5 |
| 5,718,241 A | 2/1998 | Ben-Haim et al. | 128/702 |
| 5,727,552 A | 3/1998 | Ryan | 128/653.1 |
| 5,727,553 A | 3/1998 | Saad | 128/653.1 |
| 5,729,129 A | 3/1998 | Acker | 324/207.12 |

| | | | |
|---|---|---|---|
| 5,730,129 A | 3/1998 | Darrow et al. ............ 128/653.1 |
| 5,730,130 A | 3/1998 | Fitzpatrick et al. ...... 128/653.1 |
| 5,732,703 A | 3/1998 | Kalfas et al. ............. 128/653.1 |
| 5,738,096 A | 4/1998 | Ben-Haim ............... 128/653.1 |
| 5,740,802 A | 4/1998 | Nafis et al. ............... 128/653.1 |
| 5,742,394 A | 4/1998 | Hansen ....................... 356/375 |
| 5,744,953 A | 4/1998 | Hansen .................. 324/207.17 |
| 5,748,767 A | 5/1998 | Raab .......................... 382/128 |
| 5,749,362 A | 5/1998 | Funda et al. .............. 128/653.1 |
| 5,752,513 A | 5/1998 | Acker et al. .............. 128/653.1 |
| 5,755,725 A | 5/1998 | Druais ........................ 606/130 |
| RE35,816 E | 6/1998 | Schulz ........................ 356/376 |
| 5,762,064 A * | 6/1998 | Polvani .................... 128/653.1 |
| 5,767,669 A | 6/1998 | Hansen et al. .......... 324/207.12 |
| 5,767,960 A | 6/1998 | Orman .................... 356/139.03 |
| 5,769,789 A | 6/1998 | Wang et al. ................. 600/414 |
| 5,769,843 A | 6/1998 | Abela et al. .................. 606/10 |
| 5,769,861 A | 6/1998 | Vilsmeier .................... 606/130 |
| 5,772,594 A | 6/1998 | Barrick ........................ 600/407 |
| 5,776,064 A | 7/1998 | Kalfas et al. ................ 600/414 |
| 5,782,765 A | 7/1998 | Jonkman ..................... 600/424 |
| 5,787,886 A * | 8/1998 | Kelly et al. .............. 128/653.1 |
| 5,795,294 A | 8/1998 | Luber et al. ................. 600/407 |
| 5,797,849 A | 8/1998 | Vesely et al. ............... 600/461 |
| 5,799,055 A | 8/1998 | Peshkin et al. ................ 378/42 |
| 5,800,352 A | 9/1998 | Ferre et al. .................. 600/407 |
| 5,820,553 A | 10/1998 | Hughes ....................... 600/426 |
| 5,823,958 A | 10/1998 | Truppe ........................ 600/426 |
| 5,828,770 A | 10/1998 | Leis et al. ................... 382/103 |
| 5,829,444 A | 11/1998 | Ferre et al. .................. 128/897 |
| 5,831,260 A | 11/1998 | Hansen ....................... 250/221 |
| 5,833,608 A * | 11/1998 | Acker ......................... 600/409 |
| 5,834,759 A | 11/1998 | Glossop .................... 250/203.1 |
| 5,836,954 A | 11/1998 | Heilbrun et al. ............. 606/130 |
| 5,840,025 A | 11/1998 | Ben-Haim .................. 600/424 |
| 5,848,967 A | 12/1998 | Cosman ....................... 600/426 |
| 5,851,183 A | 12/1998 | Bucholz ...................... 600/425 |
| 5,868,675 A | 2/1999 | Henrion et al. ............. 600/424 |
| 5,871,455 A | 2/1999 | Bucholz ...................... 600/407 |
| 5,873,822 A | 2/1999 | Ferre et al. .................. 600/407 |
| 5,882,304 A | 3/1999 | Ehnholm et al. ........... 600/411 |
| 5,884,410 A | 3/1999 | Prinz ............................. 33/559 |
| 5,891,034 A | 4/1999 | Bucholz ...................... 600/426 |
| 5,904,691 A | 5/1999 | Barnett et al. ............... 606/130 |
| 5,907,395 A | 5/1999 | Schulz et al. ........... 356/139.03 |
| 5,913,820 A | 6/1999 | Bladen et al. ............... 600/407 |
| 5,920,395 A | 7/1999 | Schulz ........................ 356/375 |
| 5,921,992 A | 7/1999 | Costales et al. ............. 606/130 |
| 5,938,603 A | 8/1999 | Ponzi .......................... 600/424 |
| 5,947,980 A | 9/1999 | Cosman ....................... 606/130 |
| 5,954,647 A | 9/1999 | Bova et al. .................. 600/407 |
| 5,967,982 A | 10/1999 | Barnett ........................ 600/429 |
| 5,971,997 A | 10/1999 | Guthrie et al. ............. 606/130 |
| 5,980,535 A | 11/1999 | Barnett et al. ............... 606/130 |
| 5,987,349 A | 11/1999 | Schulz ........................ 600/427 |
| 5,987,960 A | 11/1999 | Messner et al. ............. 73/1.79 |
| 5,999,837 A | 12/1999 | Messner et al. ............. 600/407 |
| 5,999,840 A | 12/1999 | Grimson et al. ............. 600/424 |
| 6,006,126 A | 12/1999 | Cosman ....................... 600/426 |
| 6,006,127 A | 12/1999 | Van Der Brug et al. .... 600/427 |
| 6,013,087 A | 1/2000 | Adams et al. ............... 606/130 |
| 6,014,580 A | 1/2000 | Blume et al. ............... 600/424 |
| 6,016,439 A | 1/2000 | Acker ......................... 600/411 |
| 6,019,725 A | 2/2000 | Vesely et al. ............... 600/447 |
| 6,175,756 B1 * | 1/2001 | Ferre et al. .................. 600/424 |

FOREIGN PATENT DOCUMENTS

| | | | | |
|---|---|---|---|---|
| DE | 19715202 A1 | 10/1998 | ........... A61B/19/00 |
| DE | 19751761 A1 | 10/1998 | ........... A61B/19/00 |
| DE | 19832296 A1 | 2/1999 | ............ G01J/1/42 |
| DE | 19747427 A1 | 5/1999 | ........... A61B/19/00 |
| EP | 0 155 857 A2 | 9/1985 | ............ G01B/7/00 |
| EP | 0 326 768 A2 | 8/1989 | ........... A61B/19/00 |
| EP | 0 359 773 B1 | 3/1990 | ............ A61B/6/02 |
| EP | 0 419 729 A1 | 4/1991 | ............ A61B/5/06 |
| EP | 0 427 358 A1 | 5/1991 | ............ A61B/6/00 |
| EP | 0 456 103 A2 | 11/1991 | ........... A61B/19/00 |
| EP | 0 469 966 A1 | 2/1992 | ........... A61B/19/00 |
| EP | 0 501 993 B1 | 9/1992 | ............ G06T/17/00 |
| EP | 0 581 704 A1 | 2/1994 | ............ A61B/8/14 |
| EP | 0 655 138 B1 | 5/1995 | ............. G01S/5/14 |
| EP | 0 894 473 A2 | 2/1999 | ............ A61B/8/12 |
| EP | 0 908 146 A2 | 4/1999 | ........... A61B/17/17 |
| EP | 0 930 046 A2 | 7/1999 | ............ A61B/6/00 |
| WO | WO 88/09151 | 12/1988 | ........... A61B/19/00 |
| WO | WO 90/05494 | 5/1990 | ........... A61B/19/00 |
| WO | WO 91/04711 | 4/1991 | ........... A61B/19/00 |
| WO | WO 91/07726 | 5/1991 | ........... G06F/15/72 |
| WO | WO 92/06645 | 4/1992 | ........... A61B/19/00 |
| WO | WO 94/04938 | 3/1994 | ............. G01S/3/14 |
| WO | WO 94/23647 | 10/1994 | ............ A61B/5/05 |
| WO | WO 94/24933 | 11/1994 | ............ A61B/5/05 |
| WO | WO 95/07055 | 3/1995 | ........... A61B/19/00 |
| WO | WO 96/11624 | 4/1996 | |
| WO | WO 96/32059 | 10/1996 | ........... A61B/5/055 |
| WO | WO 97/36192 | 10/1997 | ........... G01V/15/00 |
| WO | WO 97/49453 | 12/1997 | ............ A61N/1/36 |
| WO | WO 98/38908 | 9/1998 | ............ A61B/5/00 |
| WO | WO 99/15097 | 4/1999 | ........... A61B/19/00 |
| WO | WO 99/21498 | 5/1999 | ........... A61B/17/56 |
| WO | WO 99/23956 | 5/1999 | ........... A61B/17/17 |
| WO | WO 99/26549 | 6/1999 | ........... A61B/19/00 |
| WO | WO 99/27839 | 6/1999 | |
| WO | WO 99/29253 | 6/1999 | ........... A61B/19/00 |
| WO | WO 99/33406 | 7/1999 | ........... A61B/19/00 |
| WO | WO 99/38449 | 8/1999 | ........... A61B/19/00 |
| WO | WO 99/52094 | 10/1999 | ............ G09G/3/02 |

OTHER PUBLICATIONS

Benzel, E., et al., Magnetic Source Imaging: A Review of the Magnes System of Biomagnetic Technologies Incorporated, Neurosurgery, vol. 33, No. 2, (Aug. 1993).

Bergstrom, M., et al., Stereotaxic Computed Tomography, Am. J. Roentgenol, vol. 127 pp. 167–170 (1976).

Bucholz, R.D., et al., Variables affecting the accuracy of stereotactic localization using computerized tomography, J. Neurosurg., vol. 79, pp. 667–673 (1993).

Bucholz, R.D., et al., A Comparison of Sonic Digitizers Versus Light Emitting Diode–Based Localization, Interactive Image–guided Neurosurgery, Chapter 16, pp. 179–200 (1993).

Bucholz, R.D., et al., Intraoperative localization using a three dimensional optical digitizer, SPIE–The Intl. Soc. for Opt. Eng., vol. 1894, pp. 312–322 (Jan. 17–19, 1993).

Bucholz, R.D., et al., Image–guided surgical techniques for infections and trauma of the central nervous system, Neurosurg. Clinics of N.A., vol. 7, No. 2, pp. 187–200 (1996).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer–Assisted Surgery, Grenoble, France, pp. 459–466 (Mar. 19–22, 1997).

Bucholz, R.D., et al., Intraoperative Ultrasonic Brain Shift Monitor and Analysis, Stealth Station Marketing brochure (undated).

Cinquin, P., et al., Computer Assisted Medical Interventions, IEEE, pp. 254–263 (May/Jun. 1995).

Clarysse, P., et al., A Computer–Assisted System for 3–D Frameless Localization in Stereotaxic MRI, IEEE Trans. on Med. Imaging, vol. 10, No. 4, pp. 523–529 (Dec. 1991).

Foley, K.T., et al., Image–guided Intraoperative Spinal Localization, Intraoperative Neuroprotection, Chapter 19, pp. 325–340 (1996).

Foley, K.T., et al., The StealthStation™: Three–Dimensional Image–Interactive Guidance for the Spine Surgeon, Spinal Frontiers, pp. 7–9 (Apr. 1996).

Friets, E.M., et al., A Frameless Stereotaxic Operating Microscope for Neurosurgery, IEEE Trans. on Biomed. Eng., vol. 36, No. 6, pp. 608–617 (1989).

Gallen, C.C., et al., Intracranial Neurosurgery Guided by Functional Imaging, Surg. Neurol., vol. 42, pp. 523–530 (1994).

Galloway, R.L., et al., Interactive Image–Guided Neurosurgery, IEEE Trans. on Biomed. Eng., vol. 89, No. 12, pp. 1226–1231 (1992).

Germano, Isabelle M., et al., The NeuroStation System for Image–Guided, Frameless stereotaxy, Neurosurg., vol. 37, No. 2, pp. 348–350 (Aug. 1995).

Gomez, C.R., et al., Transcranial Doppler Ultrasound Following Closed Head Injury: Vasospasm or Vasoparalysis?, Surg. Neurol., vol. 35, pp. 30–35 (1991).

Grimson, W.E.L., et al., Virtual–reality technology is giving surgeons the equivalent of x–ray vision helping them to remove tumors . . . , Sci. Amer., vol. 280, No. 6, pp. 62–69 (Jun. 1999).

Hamadeh, A., et al., Toward automatic registration between CT and X–ray images: cooperation between 3D/2D registration and 2D edge detection, TIMC–IMAG, Faculté de Medecine de Grenoble, France, pp. 39–46 (1995)(Second Annual Intl. Symposium on Medical Robotics and Computer–Assisted Surgery, MRCAS '95, Nov. 4–7, 1995).

Hatch, J.F., Reference–Display System for the Integration of CT Scanning and the Operating Microscope, IEEE, vol. 8, pp. 252–254, Proceedings of the Eleventh Annual Northeast Bioengineering Conference (Worcester, Massachusetts) (Mar. 14–15, 1985).

Heilbrun, M.P., Computed Tomography–Guided Stereotactic Systems, Clinical Neurosurgery, Chapter 31, pp. 564–581 (1983).

Heilbrun, M.P., et al., Preliminary Experience with Brown–Roberts–Wells (BRW) computerized tomography stereotaxic guidance system, J. Neurosurg., vol. 59, pp. 217–222 (1983).

Heilbrun, M.P., et al., Stereotactic localization and Guidance Using a Machine Vision Technique, Stereotact. Funct. Neurosurg., Proceed. of the Mtg. of the Amer. Soc. for Stereot. and Funct. Neurosurg. (Pittsburgh, PA) vol. 58, pp. 94–98 (1992).

Heilbrun, M.P., Progressive Technology Applications, Neurosurgery for the Third Millenium, Chapter 15, pp. 191–198 (1992) (J. Whitaker & Sons Ltd., Amer. Assoc. of Neurol. Surgeons, Oct. 1992).

Henderson, J.M., et al., An Accurate and Ergonomic Method of Registration for Image–guided Neurosurgery, Computerized Medical Imaging and Graphics, vol. 18, No. 4, pp. 273–277 (1994).

Hofstetter, R., et al., Fluoroscopy Based Surgical Navigation–Concept and Clinical Applications, Computer Assisted Radiology and Surgery, CAR '97, Proceed. of the 11$^{th}$ Intl. Symp. and Exh., Berlin, pp. 956–960 (Jun. 25–28, 1997).

Horner, N.B., et al., A Comparison of CT–Stereotaxic Brain Biopsy Techniques, Investig. Radiol., vol. 19, pp. 367–373 (Sep.–Oct. 1984).

Kato, A., et al., A frameless, armless navigational system for computer–assisted neurosurgery, J. Neurosurg., vol. 74, pp. 845–849 (May 1991).

Klimek, L., et al., Long–Term Experience with Different Types of Localization Systems in Skull–Base Surgery, Ear, Nose & Throat Surgery, Chapter 51, pp. 635–638 (undated).

Kosugi, Y., et al., An Articulated Neurosurgical Navigation System Using MRI and CT Images, IEEE Trans. on Biomed., Eng., vol. 35, No. 2, pp. 147–152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362–366 (Jul. 3–6, 1991).

Lavallée, S., et al., A new system for computer assisted neurosurgery, IEEE EMBS, 11$^{th}$ Annual Intl. Conf., pp. 926–927 (1989).

Lavallée, S., et al., Computer Assisted Interventionist Imaging: The Instance of Stereotactic Brain Surgery, MEDINFO 89, pp. 613–617 (1989).

Lavallée, S., et al., Computer Assisted Medical Interventions, NATO ASI Series, vol. F 60, 3D Imaging in Medic., pp. 301–312 (1990).

Lavallée, S., et al., Image guided operating robot: a clinical application in stereotactic neurosurgery, IEEE Rob. and Autom. Society, Proc. of the 1992 Intl. Conf. on Rob. and Autom., May 1992, pp. 618–624, First Intl. Symp. on Med. Rob. and Comp. Assisted Surg. (Pittsburgh, PA) (Sep. 22–24, 1994).

Lavallée, S., et al., Computer Assisted Spine Surgery: a technique for accurate transpedicular screw fixation using CT data and a 3–D optical localizer, TIMC, Faculté de Medecine de Grenoble, J. of Image Guided Surg., vol. 1, No. 1, pp. 65–73 (1995).

Leavitt, D.D., et al., Dynamic Field Shaping to Optimize Stereotactic Radiosurgery, I.J. Rad. Onc. Biol. Phys., vol. 21, pp. 1247–1255 (1991).

Lemieux, L., et al., A patient–to–computed–tomography image registration method based on digitally reconstructed radiographs, Med. Phys., vol. 21, No. 11, pp. 1749–1760 (1994).

Mazier, B., et al., Computer assisted interventionist imaging: application to the vertebral column surgery, Annual Intl. Conf. of the IEEE in Medic. and Biol. Soc., vol. 12, No. 1, pp. 430–431 (1990).

Merloz, P., et al., Computer assisted Spine Surgery, Clinical Orthop. and Related Research, No. 337, pp. 86–96 (1997).

Pelizzari, C.A., et al., Accurate Three–Dimensional Registration of CT, PET, and/or MR Images of the Brain, Journal of Computer Assisted Tomography, vol. 13, No. 1, pp. 20–26 (Jan./Feb. 1989).

Penn, R.D., et al., Stereotactic Surgery with Image Processing of Computerized Tomographic Scans, Neurosurgery, vol. 3, No. 2, pp. 157–153 (Sep.–Oct. 1978).

Reinhardt, H.F., et al., Mikrochirurgische Entfernung . . . (Microsurgical removal of Deep–Seated Vascular Malformations Using Sonar Stereometry). Ultraschall in Med. 12, pp. 80–83 (1991).

Reinhardt, Hans F., Neuronavigation: A Ten–Year Review, Neurosurgery, pp. 329–341 (undated).

Reinhardt, H.F., et al., Sonic Stereometry in Microsurgical Procedures for Deep–Seated Brain Tumors and Vascular Malformations, Neurosurgery, vol. 32, No. 1, pp. 51–57 (Jan. 1993).

Roberts, D.W., et al., A frameless stereotaxic integration of computerized tomographic imaging and the operating microscope, J. Neurosurg., vol. 65, pp. 545–549 (Oct. 1986).

Simon, D.A., et al., Accuracy Validation in Image–Guided Orthopaedic Surgery, Second Annual Intl. Symp. on Med. Rob. an Comp.–Assisted Surgery, MRCAS '95, pp. 185–192 (1995).

Smith, K.R., et al., Multimodality Image Analysis and Display Methods for Improved Tumor Localization in Stereotactic Neurosurgery, Annual Intl. Conf. of the IEEE Eng. in Med. and Biol. Soc., vol. 13, No. 1, p. 210 (1991).

Smith, K.R., et al., Computer Methods for Improved Diagnostic Image Display Applied to Stereotactic Neurosurgery, Automedical, vol. 14, pp. 371–386 (1991).

Smith, K.R., et al., The Neurostation™—a highly, accurate, minimally invasive solution to frameless stereotatic neurosurgery, Comput. Med. Imag. and Graph., vol. 18, No. 4, pp. 247–256 (1994).

Stereotactic One, Affordable PC Based Graphics for Stereotactic Surgery, Stereotactic Image Systems, Inc. (SLC, Utah) (marketing brochure, undated).

BrainLab marketing brochures for Vector Vision (undated) (26 pages).

The Laitinen Stereoadapter 5000, Instructions for use, by Surgical Navigation Technologies, FDA–NS–001A Rev. 0 (undated).

Pixsys 3–D Digitizing Accessories, by Pixsys (marketing brochure, undated).

* cited by examiner

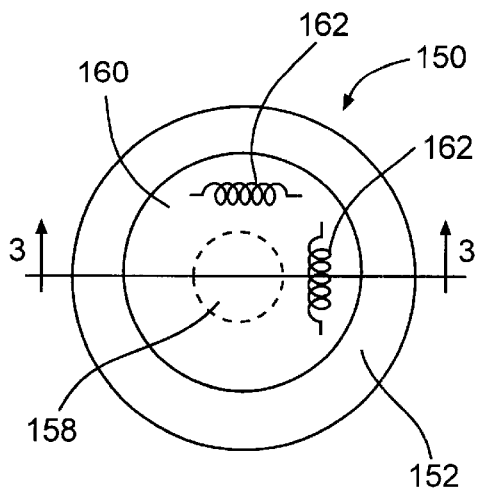
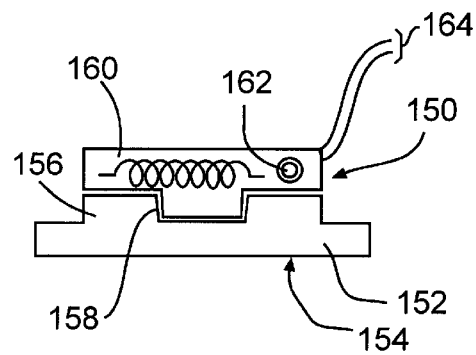
FIG. 2      FIG. 3
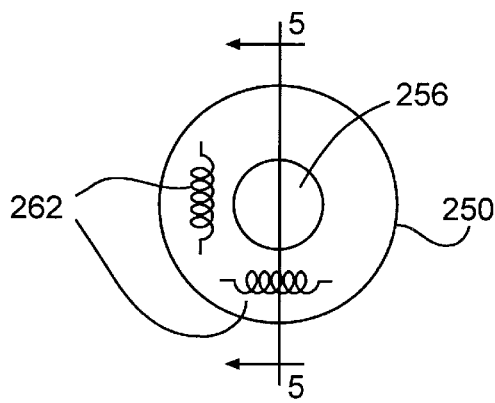
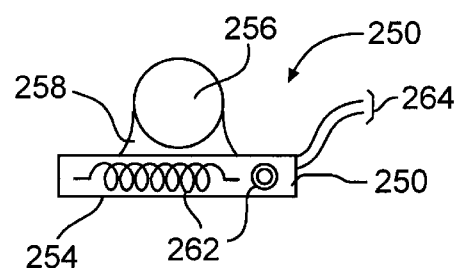
FIG. 4      FIG. 5

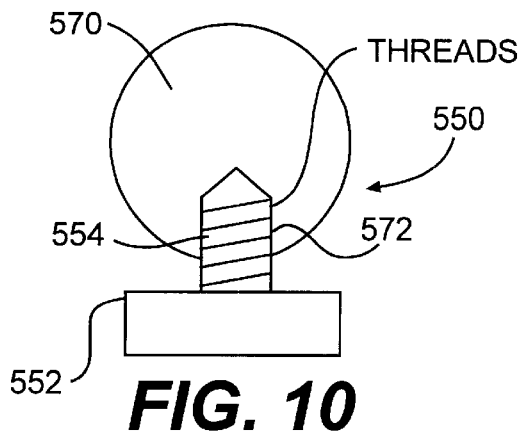
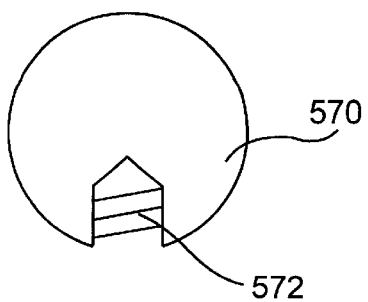
FIG. 10
FIG. 11
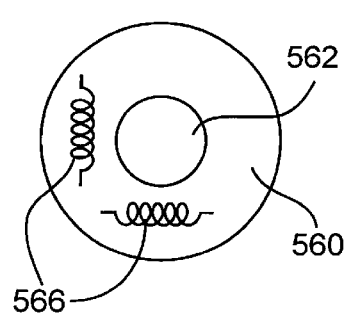
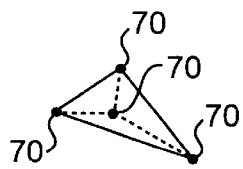
FIG. 12
FIG. 13
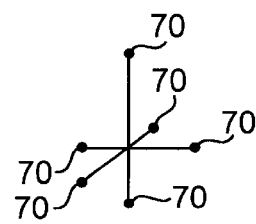
FIG. 14
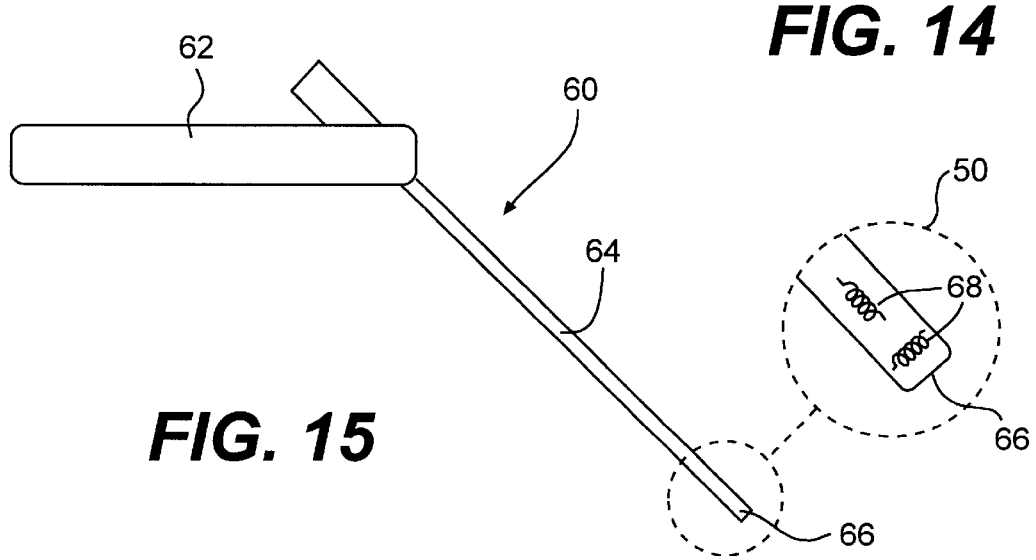
FIG. 15

REGISTRATION OF HUMAN ANATOMY INTEGRATED FOR ELECTROMAGNETIC LOCALIZATION

CONCURRENTLY FILED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; Surgical Communication and Power System, by Mark W. Hunter, Paul Kessman and Brad Jascob; and Surgical Sensor, by Mark W. Hunter, Sheri McCoid and Paul Kessman.

BACKGROUND OF THE INVENTION

1. Field of the Invention

The present invention relates to localization of a position during neurosurgery. The present invention relates more specifically to electromagnetic localization of a position during stereotactic neurosurgery, such as brain surgery and spinal surgery.

2. Description of Related Art

Precise localization of a position is important to stereotactic neurosurgery. In addition, minimizing invasiveness of surgery is important to reduce health risks for a patient. Stereotactic surgery minimizes invasiveness of surgical procedures by allowing a device to be guided through tissue that has been localized by preoperative scanning techniques, such as for example, MR, CT, ultrasound, fluoro and PET. Recent developments in stereotactic surgery have increased localization precision and helped minimize invasiveness of surgery.

Stereotactic neurosurgery is now commonly used in neurosurgery of the brain. Such methods typically involve acquiring image data by placing fiducial markers on the patient's head, scanning the patient's head, attaching a headring to the patient's head, and determining the spacial relation of the image data to the headring by, for example, registration of the fiducial markers. Registration of the fiducial markers relates the information in the scanned image data for the patient's brain to the brain itself, and involves one-to-one mapping between the fiducial markers as identified in the image data and the fiducial markers that remain on the patient's head after scanning and throughout surgery. This is referred to as registering image space to patient space. Often, the image space must also be registered to another image space. Registration is accomplished through knowledge of the coordinate vectors of at least three non-collinear points in the image space and the patient space.

Currently, registration for image guided surgery can be completed by different methods. First, point-to-point registration is accomplished by identifying points in image space and then touching the same points in patient space. Second, surface registration involves the user's generation of a surface (e.g., the patient's forehead) in patient space by either selecting multiple points or scanning, and then accepting or rejecting the best fit to that surface in image space, as chosen by the processor. Third, repeat fixation devices entail the user repeatedly removing and replacing a device in known relation to the fiducial markers. Such registration methods have additional steps during the procedure, and therefore increase the complexity of the system and increase opportunities for introduction of human error.

It is known to adhere the fiducial markers to a patient's skin or alternatively to implant the fiducial markers into a patient's bone for use during stereotactic surgery. For example, U.S. Pat. No. 5,595,193 discloses an apparatus and method for creating a hole that does not penetrate the entire thickness of a segment of bone and is sized to accommodate a fiducial marker. A fiducial marker may then be inserted into the hole and image data may be acquired.

Through the image data, quantitative coordinates of targets within the patient's body can be specified relative to the fiducial markers. Once a guide probe or other instrument has been registered to the fiducial markers on the patient's body, the instrument can be navigated through the patient's body using image data.

It is also known to display large, three-dimensional data sets of image data in an operating room or in the direct field of view of a surgical microscope. Accordingly, a graphical representation of instrument navigation through the patient's body is displayed on a computer screen based on reconstructed images of scanned image data.

Although scanners provide valuable information for stereotactic surgery, improved accuracy in defining the position of the target with respect to an accessible reference location can be desirable. Inaccuracies in defining the target position can create inaccuracies in placing a therapeutic probe. One method for attempting to limit inaccuracies in defining the target position involves fixing the patient's head to the scanner to preserve the reference. Such a requirement is uncomfortable for the patient and creates other inconveniences, particularly if surgical procedures are involved. Consequently, a need exists for a system utilizing a scanner to accurately locate positions of targets, which allows the patient to be removed from the scanner.

Stereotactic neurosurgery utilizing a three-dimensional digitizer allows a patient to be removed from the scanner while still maintaining accuracy for locating the position of targets. The three-dimensional digitizer is used as a localizer to determine the intra-procedural relative positions of the target. Three-dimensional digitizers may employ optical, acoustic, electromagnetic, conductive or other known three-dimensional navigation technology for navigation through the patient space.

Stereotactic surgery techniques are also utilized for spinal surgery in order to increase accuracy of the surgery and minimize invasiveness. Accuracy is particularly difficult in spinal surgery and must be accommodated in registration and localization techniques utilized in the surgery. Prior to spinal surgery, the vertebra are scanned to determine their alignment and positioning. During imaging, scans are taken at intervals through the vertebra to create a three-dimensional pre-procedural data set for the vertebra. After scanning the patient is moved to the operating table, which can cause repositioning of the vertebra. In addition, the respective positions of the vertebra may shift once the patient has been immobilized on the operating table because, unlike the brain, the spine is not held relatively still in the same way as a skull-like enveloping structure. Even normal patient respiration may cause relative movement of the vertebra.

Computer processes discriminate the image data retrieved by scanning the spine so that the body vertebra remain in memory. Once the vertebra are each defined as a single rigid body, the vertebra can be repositioned with software algorithms that define a displaced image data set. Each rigid body element has at least three fiducial markers that are visible on the pre-procedural images and accurately detectable during the procedure. It is preferable to select reference points on the spinous process that are routinely exposed during such surgery. See also, for example, U.S. Pat. No. 5,871,445, WO 96/11624, U.S. Pat. No. 5,592,939 and U.S. Pat. No. 5,697,377, the disclosures of which are incorporated herein by reference.

SUMMARY OF THE INVENTION

To enhance the prior art, and in accordance with the purposes of the invention, as embodied and broadly described herein, there is provided a system for displaying relative positions of two structures during a procedure on a body. The system comprises memory for storing an image data set representing the position of the body based on scans of the body, the image data set having a plurality of data points in known relation to a plurality of reference points for the body; a magnetic field generator for generating a magnetic field to be sensed by one or more magnetic field sensors placed in known relation to the reference points of the body for detecting the magnetic field and for generating positional signals in response to the detected magnetic field; a processor for receiving the reference signals and for ascertaining a location of the magnetic field sensors based upon the reference signals, the processor for generating a displaced image data set representing the relative positions of the body elements during the procedure; and a display utilizing the displaced image data set generated by the processor to display the relative position of the body elements during the procedure.

The present invention also provides a method for use during a procedure on a body. The method generates a display representing relative positions of two structures during the procedure. The method comprises the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

The present invention further includes a device for use in a system for displaying relative positions of two structures during a procedure on a body. The device comprises a base adapted for attachment to the body, a fiducial marker mounted to the base, and a sensor having a known location and orientation with respect to the fiducial marker.

Additional features and advantages of the invention will be set forth in the description which follows, and in part will be apparent from the description, or may be learned from practice of the invention. The objectives and other advantages of the invention will be realized and attained by the apparatus particularly pointed out in the written description and claims herein as well as the appended drawings.

BRIEF DESCRIPTION OF THE DRAWINGS

The accompanying drawings, which are incorporated in and constitute part of the specification, illustrate a presently preferred embodiment of the invention and together with the general description given above and detailed description of the preferred embodiment given below, serve to explain the principles of the invention.

FIG. 2 illustrates a top view of a first embodiment of a fiducial marker-sensor device;

FIG. 3 illustrates a cross-sectional view of the first embodiment of the fiducial marker-sensor device of the present invention, taken along line 3—3 of FIG. 2;

FIG. 4 illustrates a top view of a second embodiment of a fiducial marker-sensor device;

FIG. 5 illustrates a cross-sectional view of the second embodiment of the fiducial marker-sensor device of the present invention, taken along line 5—5 of FIG. 4;

FIG. 10 illustrates a side view of a fifth embodiment of a fiducial marker-sensor device of the present invention;

FIG. 11 illustrates a side view of a fiducial marker according to the fifth embodiment of the fiducial marker-sensor device of the present invention;

FIG. 12 illustrates a side view of sensor ring according to the fifth embodiment of the fiducial marker-sensor device of the present invention;

FIG. 13 illustrates a schematic view of a sixth embodiment of a fiducial marker-sensor device of the present invention;

FIG. 14 illustrates a schematic view of a seventh embodiment of a fiducial marker-sensor device of the present invention;

FIG. 15 illustrates a medical instrument for use in the registration system of the present invention.

DESCRIPTION OF THE PREFERRED EMBODIMENTS

Reference will now be made in detail to the present preferred exemplary embodiments of the invention, examples of which are illustrated in the accompanying drawings. Wherever possible, the same reference numbers will be used throughout the drawings to refer to the same or like parts.

In accordance with the present invention, a method for use during a procedure on a body generates a display representing relative positions of two structures during the procedure. The method comprises the steps of (i) storing an image data set in memory, the image data set representing the position of the body based on scans taken of the body prior to the procedure; (ii) reading the image data set stored in the memory, the image data set having a plurality of data points in known relation to a plurality of reference points for at least one of the two structures; (iii) placing one or more magnetic field sensors in known relation to the reference points of the two structures; (iv) generating a magnetic field; (v) detecting the magnetic field with the magnetic field sensors; (vi) ascertaining the locations of the sensors based upon the magnetic field detected by the sensors and processing the locations of the sensors to generate a displaced image data set representing the relative position of the two structures during the procedure; and (vii) generating a display based on the displaced image data set illustrating the relative position of the two structures during the procedure. The relation of the plurality of data points to the plurality of reference points is determined by the user or by standard image processing of shape detection.

The two structures can be body elements (e.g., vertebrae of the spine) or a body element (e.g., a brain or a vertebrae) and a medical instrument such as a probe.

Figure 1:
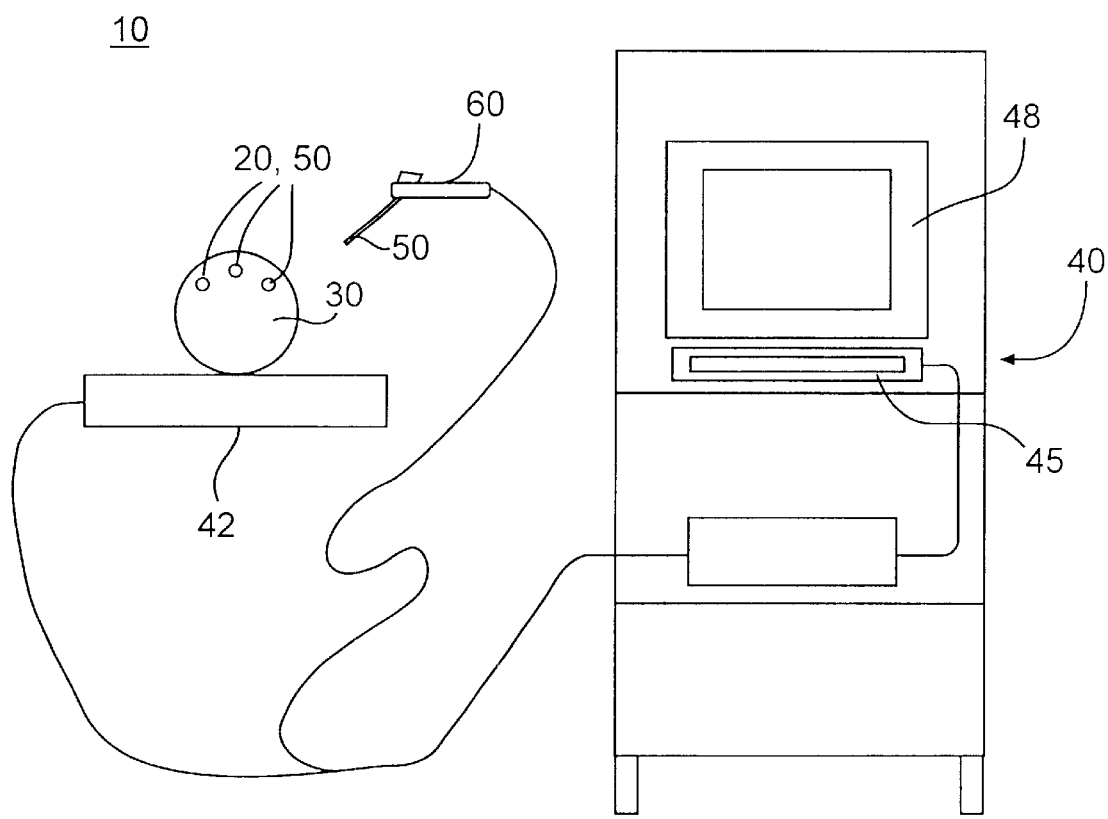
FIG. 1 is a schematic diagram illustrating an embodiment of the registration system of the present invention.

FIG. 1 schematically illustrates an exemplary embodiment of the registration system 10 of the present invention. For illustrative purposes, the registration system of the present invention will be described for a brain surgery procedure. However, the registration system may alternatively be used for a number of different procedures on the body, including spinal surgery (described hereinafter).

Initially, at least one fiducial marker 20 is placed on patient's head 30. A pre-operative scan is taken of the patient's head 30, preferably using at least one of MR, CT, ultrasound, fluoro and PET. The scan generates an image data set that is placed into the memory of a computer system 40. The image data set represents the position of the patient's head 30 based on the pre-operative scans of the head. The image data set includes a plurality of data points.

During the procedure, at least one magnetic field sensor 50 is placed in known relation to the at least one fiducial marker 20 on the patient's head 30. For example, the magnetic field sensor can be integrated with the fiducial marker, attached to the fiducial marker, or interchanged with the fiducial marker. Another magnetic field sensor 50 can be placed, for example, in a medical instrument 60. The medical instrument 60 does not need a fiducial marker because it is not present in the scan taken to create the image data set.

During the procedure, a magnetic field generator (not shown) generates a magnetic field in the area of the patient. For example, coils (not shown) can be embedded into an operating table 42 on which the patient is placed. The magnetic field sensors 50 on the patient's head 30 and in the medical instrument 60 detect the generated magnetic field and send appropriate signals to the processor 45 so that the processor 45 can determine the positions of the magnetic field sensors 50 during the procedure. Once the processor 45 determines the positions of the magnetic field sensors 50 on the patient's head 30, the position of the magnetic field sensors 50 on the patient's head is registered to the position of the fiducial markers 20 as represented in the scan.

After the position of the magnetic field sensors 50 has been determined and the sensors on the patient's head 30 are registered, a displaced image data set is created and displayed on a monitor 48. The display includes the relative position of the medical device 60 to the patient's head 30.

A variety of fiducial markers 20 and magnetic field sensors 50 (combined to create "fiducial marker-sensor devices") are illustrated in FIGS. 2 through 14. In FIGS. 2 and 3, an interchangeable fiducial marker-sensor device 150 is illustrated. The device 150 includes a base 152 that is attached to the patient. The base 152 is preferably adhesively attached to the patient along its bottom surface 154, but may also be implanted in the patient, clamped or stapled to the patient, or otherwise suitably attached to the patient. The base 152 has a raised ring portion 156 and a central circular depression 158. A fiducial (not shown) having a shape complementary to the base 152 is placed into the base for scanning, and then a sensor 160 having a shape complementary to the base 152 is placed in the base for electromagnetic tracking of the patient space. One or more coils 162 are placed in the sensor 160, preferably perpendicular to each other. The coils 162 are placed in communication with the processor 45, for example using wires 164 or similarly suitable communication links such as radio waves. Alternatively, optical, acoustic or inertial elements could be interchanged for the sensor if an optical, acoustic or inertial navigation system is employed.

In FIGS. 4 and 5, a preferred embodiment of an integrated fiducial marker-sensor 250 is illustrated. The illustrated fiducial marker 256 is spherical, but provides only location data and no orientation data. The device 250 includes a base 252 that is attached to the patient. The base 252 is preferably adhesively attached to the patient along its bottom surface 254, but may also be implanted in the patient, clamped or stapled to the patient, or otherwise suitably attached to the patient. The fiducial marker 256 is attached to the base 252, for example using an epoxy or plastic layer 258. The base is also a sensor for electromagnetic tracking of the patient space. One or more coils 262 are placed in the base 252, preferably perpendicular to each other. The coils 262 are placed in communication with the processor 45, for example using wires 264 or other suitable communication links such as radio waves. Alternatively, optical, acoustic or inertial elements known in the art could be interchanged for the sensor if an optical, acoustic or inertial navigation system is employed.

The preferred size of the spherical fiducial marker is dependent upon scan slice thickness. For example, with 1 mm slices, a 3 mm sphere is preferred and for 3 mm slices an 8 mm sphere is preferred. As can be see in FIGS. 3 and 4, the spherical fiducial marker 256 is spaced from the base. It is preferable (but not necessary) that the space between the fiducial marker and the patient is greater than the slice thickness to provide a "barrier." By barrier, the present invention contemplates that the fiducial is preferably spaced from the patient's skin by a large enough distance that the fiducial and the skin do not blend together in the scan image and appear as one object.

Figure 6:
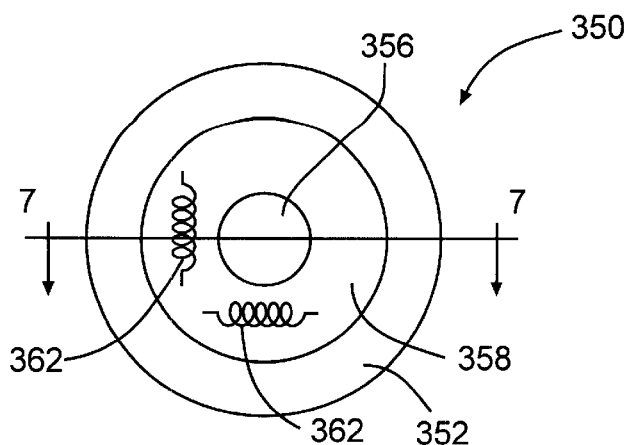
FIG. 6 illustrates a top view of a third embodiment of a fiducial marker-sensor device.
Figure 7:
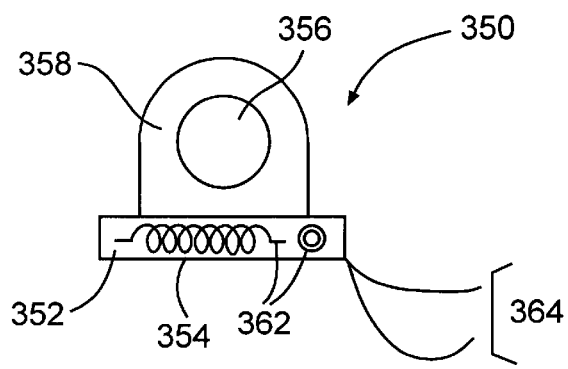
FIG. 7 illustrates a cross-sectional view of the third embodiment of the fiducial marker sensor device of the present invention, taken along line 7—7 of the FIG. 6.

In FIGS. 6 and 7, another preferred embodiment of an integrated fiducial marker-sensor 350 is illustrated. The illustrated fiducial marker 356 has a spherical shape. The device 350 includes a base 352 that is attached to the patient either adhesively along its bottom surface 354, implanted in the patient, clamped or stapled to the patient, or otherwise suitably attached to the patient. The fiducial marker 356 is attached to the base 352, for example using an epoxy or plastic casing 358. The base is also a sensor for electromagnetic tracking of the patient space. One or more coils 362 are placed in the base 352, preferably perpendicular to each other. The coils 362 are placed in communication with the processor 45, for example using wires 364. Alternatively, optical, acoustic or inertial elements could be interchanged for the sensor if an optical, acoustic or inertial navigation system is employed.

As stated above, the preferred size of the spherical fiducial marker is dependent upon scan slice thickness, and the spherical fiducial marker 356 is preferably (but not necessarily) spaced from the base a distance greater than the slice thickness to provide a barrier.

Figure 8:
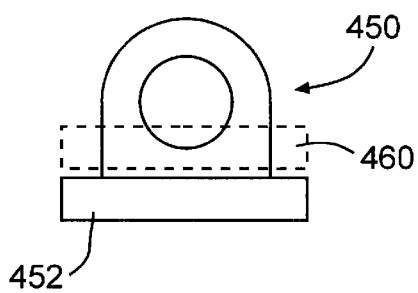
FIG. 8 illustrates a side view of a fourth embodiment of a fiducial marker-sensor device of the present invention, indicating a placement of an attachable sensor ring in phantom.
Figure 9:
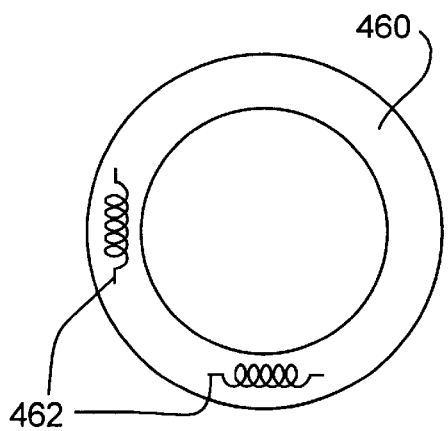
FIG. 9 illustrates a top view of an attachable sensor ring for placement according to the fourth embodiment of the fiducial-sensor device as illustrated in FIG. 4.

FIGS. 8 and 9 illustrate a fiducial marker-sensor device 450 similar to the fiducial marker-sensor device illustrated in FIGS. 6 and 7, except that the sensor is in an attachable ring 460 instead of being in the base 452. This embodiment allows attachment of the sensor in known relation to the fiducial after scanning has taken place. As with the above-described embodiments, the sensor includes at least one sensor 462, and preferably includes two perpendicularly oriented sensors 462.

FIGS. 10 through 12 illustrate an interchangeable fiducial marker-sensor device 550 including a base 552 having a protrusion 554 that is threaded. A fiducial marker 570 has a complementary threaded recess 572 for engagement with the protrusion 554 on the base 552. FIG. 11 illustrates the fiducial marker 570. FIG. 12 illustrates a sensor ring 560 with an aperture 562 that is threaded so that it can be interchanged with the fiducial marker 570 on the base 552. Alternatively, this embodiment could also employ a recess in the base and a complementary protrusion on the interchangeable fiducial marker and sensor ring.

The present invention contemplates use of a fiducial marker having a unique geometrical shape in any of the embodiments of the fiducial marker-sensor device described hereinabove. In addition, the present invention contemplates placement of multiple fiducial markers on the patient and attachment of sensors to a subset of the fiducial markers that the user finds are most clearly and helpfully represented in the scan. Placement of additional sensors helps ensure that a proper number of sensors can be placed on the patient even if one or more fiducial markers are not clearly identifiable in the scan.

One exemplary embodiment of the method of the present invention utilizes at least one fiducial marker-sensor device. The user places at least one fiducial marker with a unique geometric shape on the patient's head 30. One example of the unique geometrical shape contemplated by the present invention includes at least three distinct non-collinear points, and may include more points to increase the accuracy of the system in correlating patient space to image space. Examples of presently preferred unique geometric shapes including more than three non-collinear points are illustrated in FIGS. 13 and 14. Unique geometrical shapes allows determination of both the location and the orientation of the fiducial marker from the image slices and with a six degree of freedom (DOF) sensor. The image slices represent the location and orientation of the at least one fiducial marker in image space and the six DOF sensor determines the corresponding location and orientation of the at least one fiducial marker in patient space to accomplish auto-registration. The six DOF sensor is preferably electromagnetic, but may also be acoustic, optical or inertial. Other uniquely identifiable shapes can be used, for example a T-shape or a tack.

Alternatively, the user may place at least two fiducial markers with predetermined geometrical shapes (see FIGS. 13 and 14) on the patient's head 30. The location and orientation of the fiducial markers can be determined from the image slices and with a five DOF sensor. A six DOF sensor is not needed, but can be used, when at least two fiducial markers with unique geometries are used. The image slices represent the location and orientation of the fiducial markers in image space and the five DOF sensor determines the corresponding location and orientation of the fiducial markers in patient space to accomplish auto-registration. The five DOF sensor is preferably electromagnetic, but may also be acoustic, optical or inertial.

As another alternative, the user may place at least three fiducial markers on the patient's head 30. The location of the fiducial markers can be determined from the image slices and with a combination of sensors to define six DOF (e.g., two five DOF sensors). The image slices represent at least the location of the fiducial markers in image space and the sensor determines at least the corresponding location of the fiducial markers in patient space to accomplish auto-registration. The sensors are preferably electromagnetic.

In yet another alternative, the user may place at least three fiducial markers on the patient's head 30. In this embodiment including at least three fiducial markers, the fiducial markers need not have a unique geometrical shape. Exemplary embodiments of fiducial markers that do not have a unique geometrical shape are illustrated in FIGS. 4 through 9. The exemplary fiducial marker-sensor devices illustrated in FIGS. 4 through 9 include a spherical fiducial marker. The location of the fiducial markers can be determined from the image slices and with a three DOF sensor. A three DOF sensor is commonly used in both acoustic, optical or inertial navigation systems. The image slices represent the location of the fiducial markers in image space and the three dimensional sensor determines the corresponding location of the fiducial markers in patient space to accomplish auto-registration.

As stated above, once fiducial markers 20 have been placed on the patient's head, image slices or a three-dimensional scan (e.g., MR, CT, ultrasound, fluoro and PET) are taken of the patient's head to create a three-dimensional data set having data points corresponding to reference points on the fiducial marker(s) 20. The relation of the plurality of data points to the plurality of reference points is determined by the user or by standard image processing of shape detection. The scan is preferably taken prior to or during the procedure. An image data set is created by the scan and placed in computer memory, and the processor 45 identifies the fiducial marker(s) in image space (in the image data set) using image algorithms. Each fiducial marker is represented by at least one data point in the image data set.

Preferably, the image data set is created prior to placing the patient on the operating table. Once the patient is ready for surgery, the processor 45 can identify the fiducial marker(s) 20 in patient space using signals received from the sensors 50 on the patient's head 30. Each fiducial marker includes least one reference point 70 in patient space (see exemplary fiducial markers illustrated in FIGS. 13 and 14). The reference points need not be attached to a defined triangle as illustrated in FIG. 13, but instead may be as simple as 3 suspended BBs. The reference points in patient space correlate to the data points in the image data set. The signals sent by the sensors to the processor 45 to identify the fiducial marker(s) in patient space are called "localization information" and allow the processor to "auto-register" the patient by correlating the reference points to the data points. The relation of the plurality of data points to the plurality of reference points is determined by the user or by standard image processing of shape detection. This is done by determining a translation matrix between image space and patient space.

Auto-registering the patient provides a simplified and more user-friendly system because the user need not select the data points in the data set and thereafter touch fiducial markers, or create a surface in patient space by selecting multiple points or scanning and then accept or reject the best fit in image space as determined by the processor, or repeatedly remove and replace a localizing device. In addition, accuracy can be enhanced because opportunities for human error during user registration is eliminated.

During the procedure, at least one sensor 50 is placed in known relation to the fiducial marker(s) 20 on patient's head to create a dynamic reference frame for the procedure. Preferably, the at least one sensor is integrated with the fiducial marker(s), removably attached to the fiducial marker(s), permanently affixed to the fiducial marker(s) after the patient is scanned, or interchanged with the fiducial marker(s) during the procedure. In a preferred embodiment of the invention in which a single uniquely shaped fiducial marker with ascertainable location and orientation is utilized (see FIGS. 13 and 14), the location and orientation of the sensor with respect to the fiducial marker is determined prior to placement of the fiducial marker-sensor onto the patient and remains constant throughout the procedure. For example, factory calibration may be used.

During the procedure, the computer system dynamically tracks movement of the sensors 50 on the patient's head 30 and on the medical instrument 60. Thus, the system tracks movement of the medical instrument 60 relative to the patient's head 30. In addition, the system can "learn the geometry" of sensors placed on the patient's head to perform geometry checks that help maintain system accuracy. To learn the geometry of the sensors 50 on the patient's head, the processor 45 determines the relative locations of all of the sensors 50 on the patient's head. The relative locations of the sensors on the patient's head should not change. If the processor determines that the relative location of sensors on the patient's head has changed, the system indicates to the user that an error may have occurred. By using the magnetic field sensors as a dynamic reference frame, the system need not employ additional navigational devices in the surgical field.

As the system tracks relative movement of two structures such as the patient's head and the medical instrument, a graphical representation of instrument navigation through the patient's brain is displayed on a monitor 48 of the computer system 40 based on reconstructed images of scanned image data.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68 that makes up the sensor 50. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

When using the registration system of the present invention during spinal surgery, the systems ability to track relative movement of multiple structures is particularly important for at least the following reason. Prior to spinal surgery, the vertebra are scanned to determine their alignment and positioning. During imaging, scans are taken at intervals through the vertebra to create a three-dimensional pre-procedural data set for the vertebra. However, after scanning the patient must be moved to the operating table, causing repositioning of the vertebra. In addition, the respective positions of the vertebra may shift once the patient has been immobilized on the operating table because, unlike the brain, the spine is not held relatively still by a skull-like enveloping structure. Even normal patient respiration may cause relative movement of the vertebra.

Figure 16:
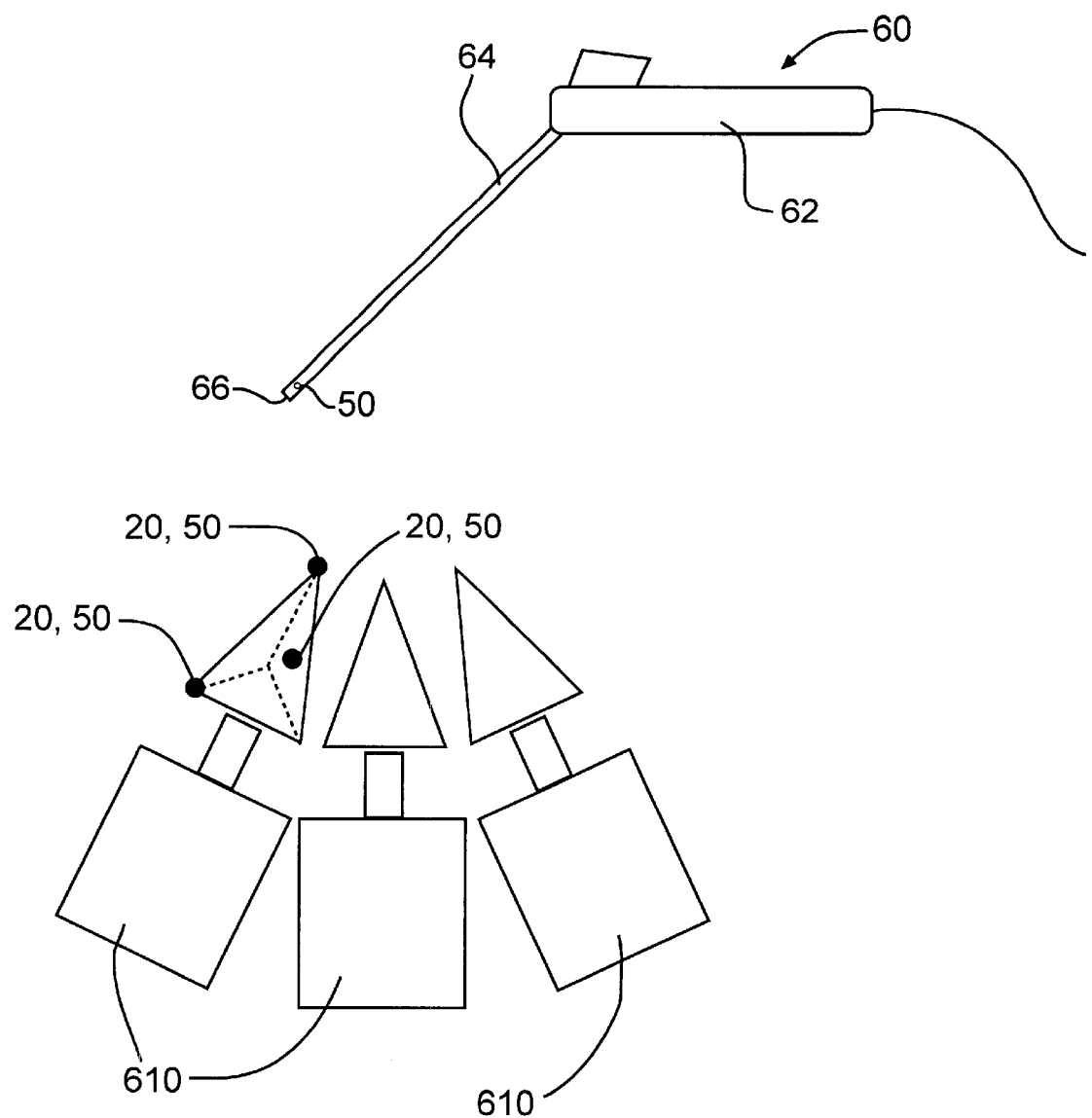
FIG. 16 schematically illustrates the registration system for use in spinal procedures.

FIG. 16 schematically illustrates elements of spinal surgery needed to explain the procedures of the present invention. At least one fiducial marker 20 is placed on each vertebra 610 of concern during the procedure. A vertebra "of concern" is a vertebra whose position the user is concerned with during the spinal procedure. Once at least one fiducial marker 20 has been placed on each vertebra of concern, image slices or a three-dimensional scan (e.g., MR, CT, ultrasound, fluoro and PET) are taken of the patient's spine to create a three-dimensional data set having data points corresponding to reference points on each fiducial marker 20. The relation of the plurality of data points to the plurality of reference points is determined by the user or by standard image processing of shape detection. The scan is preferably taken prior to or during the procedure. An image data set is created by the scan and placed in computer memory, and the processor 45 (see FIG. 1) identifies each fiducial marker 20 in image space (in the image data set) using image algorithms. Each fiducial marker 20 is represented by at least one data point in the image data set.

Preferably, the image data set is created prior to placing the patient on the operating table. Once the patient is ready for surgery, the processor 45 can identify the fiducial marker 20 in patient space using signals received from at least one sensor 50, placed in known relation to the fiducial marker(s) 20 placed on the patient's vertebra 610. As described above, the system then auto-registers the patient by correlating the reference points to the data points. According to the present invention, the fiducial marker-sensor devices illustrated with respect to brain surgery are equally acceptable for spinal surgery.

During the procedure, the computer system dynamically tracks movement of each sensor 50 on the patient's vertebra and on the medical instrument 60. Thus, the system tracks alignment and positioning of the vertebra 610 (e.g., relative movement of the vertebra) as well as movement of the medical instrument 60 relative to the vertebrae. In addition, the system can "learn the geometry" of sensors placed on a single to perform geometry checks that help maintain system accuracy as described above.

As the system tracks relative movement of vertebra 610 and the medical instrument 60, a graphical representation of instrument navigation through the patient's spinous process is displayed on a monitor 48 of the computer system 40 based on reconstructed images of scanned image data.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

It will be apparent to those skilled in the art that various modifications and variations can be made in the registration system of the present invention and in construction of this registration system without departing from the scope or spirit of the invention. As an example a variety of other embodiments of the fiducial marker-sensor device could be employed, including fiducial markers of an endless variety of shapes and sizes. The magnetic field generator and sensor roles could be reversed, such that the operating table 42 could include a sensor, and field generators could be placed on the patient and in the medical device. In addition, an optical, acoustic or inertial system could be used to track the location of the sensors and fiducial markers instead of electromagnetics.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for displaying positions of a body element relative to a structure during a procedure on the body, the system comprising:

memory for storing an image data set representing the position of the body element based on scans of the body element, the image data set having a plurality of data points in known relation to a plurality of reference points for the body element;

a magnetic field generator for generating a magnetic field to be sensed by one or more magnetic field sensors placed in known and constant relation to the reference points of the body element and one or more magnetic field sensors placed on the structure for detecting the magnetic field and for generating positional signals in response to the detected magnetic field;

a processor for receiving the signals from the magnetic field sensors and for ascertaining a location of the magnetic field sensors based upon the received signals, the processor auto-registering the position of the reference points of the body element with the known and constant position of the one or more magnetic field sensors associated with the body element to generate a displaced image data set representing the relative positions of the body element and the structure during the procedure; and a display utilizing the displaced image data set generated by the processor to display the relative position of the body element and the structure during the procedure, wherein said processor dynamically tracks movement of the body element relative to the structure.

2. The system of claim 1, wherein the magnetic field generator includes components for generating a plurality of magnetic fields.

3. The system of claim 1, wherein the structure includes a body element.

4. The system of claim 3, wherein the body element is a vertebrae.

5. The system of claim 1, wherein the structure is a medical instrument.

6. The system of claim 5, wherein the body element is a brain.

7. The system of claim 6, wherein the data points of the image data set are determined using image processing selected from the group consisting of MR, CT, ultrasound, fluoro and PET.

8. A method for use during a procedure on a body, the method generating a display representing relative positions of two structures during the procedure, the method comprising:

storing an image data set in memory, the image data set representing the position of the body based on scans taken of the body prior to the procedure;

reading the image data set stored in the memory, the image data set having a plurality of data points in known relation to a plurality of reference points for at least one of the two structures;

placing one or more first magnetic field sensors in known and constant relation to the reference points of one of the two structures;

placing one or more second magnetic field sensors in relation to the other one of the two structures;

generating a magnetic field;

detecting the magnetic field with the first and second magnetic field sensors;

ascertaining the locations of the first and second magnetic field sensors based upon the magnetic field detected by the first and second magnetic field sensors and auto-registering the locations of the first magnetic field sensors with the locations of the reference points to generate a displaced image data set representing the relative position of the two structures during the procedure;

generating a display based on the displaced image data set illustrating the relative position of the two structures during the procedure; and dynamically tracking movement of the relative position of the two structures during the procedure.

9. The method of claim 8, wherein the image data set is determined using image processing selected from the group consisting of MR, CT, ultrasound, fluoro and PET.

10. The method of claim 8, wherein generating the magnetic field includes generating a plurality of magnetic fields.

11. The method of claim 8, wherein the two structures include body elements.

12. The method of claim 11, wherein the body elements are vertebrae.

13. The method of claim 8, wherein the two structures include a body element and a medical instrument.

14. The method of claim 13, wherein the body element includes a brain.

15. A system for use in displaying a position of a first structure relative to a second structure during a procedure on a body, said system comprising:

at least one fiducial marker positioned relative to the first structure;

memory operable to store an image data set representing a position of the first structure, said image data set having a plurality of data points with said at least one fiducial marker represented by at least one of said data points;

a magnetic field generator operable to generate a magnetic field;

a first magnetic field sensor associated with the first structure and placed in a known and constant relation to said at least one fiducial marker, said first magnetic field sensor operable to detect said magnetic field and generate positional signals in response to said detected magnetic field;

a second magnetic field sensor associated with the second structure, said second magnetic field sensor operable to detect said magnetic field and generate positional signals in response to said detected magnetic field;

a processor operable to ascertain a location of said first and second magnetic field sensors from said positional signals generated by said first and second magnetic field sensors, said processor further operable to auto-register the position of said at least one fiducial marker with the position of said first magnetic field sensor to create a dynamic reference frame to generate a displaced image data set representing relative positions of the first and second structures; and a display operable to use said displaced image data set generated by said processor to display positions of the first structure relative to the second structure, wherein said processor dynamically tracks movement of said first magnetic field sensor associated with said at least one fiducial marker and the first structure relative to the second magnetic field sensor associated with the second structure.

16. The system as defined in claim 15 wherein the first structure is a body element and the second structure is a medical instrument.

17. The system as defined in claim 16 wherein the body element is a brain.

18. The system as defined in claim 15 wherein the first structure is a first body element and the second structure is a second body element.

19. The system as defined in claim 18 wherein the first body element is a first vertebrae and the second body element is a second vertebrae.

20. The system as defined in claim 15 further comprising a plurality of first magnetic field sensors associated with the first structure and placed in known and constant relationship to a plurality of fiducial markers positioned relative to the first structure.

21. The system as defined in claim 20 wherein said processor is further operable to learn the geometry of the plurality of first magnetic field sensors associated with the first structure to perform geometry checks to maintain system accuracy by determining if a relative location of said plurality of first magnetic field sensors associated with the first structure has changed, whereby said processor notifies a user that an error may have occurred.

* * * * *